(12) United States Patent
Shin et al.

(10) Patent No.: US 12,274,708 B2
(45) Date of Patent: Apr. 15, 2025

(54) COMPOSITION FOR AMELIORATING OR TREATING DEMENTIA CONTAINING 2'-FUCOSYLLACTOSE

(71) Applicant: Advanced Protein Technologies Corp., Suwon-si (KR)

(72) Inventors: Chul Soo Shin, Suwon-si (KR); Jong Won Yoon, Seongnam-si (KR); Seon Min Jeon, Daegu (KR); Young Ha Song, Yongin-si (KR); Jong Gil Yoo, Pyeongtaek-si (KR); Jeong Su Bang, Ansan-si (KR)

(73) Assignee: Advanced Protein Technologies Corp., Suwon-si (KR)

( * ) Notice: Subject to any disclaimer, the term of this patent is extended or adjusted under 35 U.S.C. 154(b) by 0 days.

(21) Appl. No.: 18/508,838

(22) Filed: Nov. 14, 2023

(65) Prior Publication Data
US 2024/0173341 A1    May 30, 2024

Related U.S. Application Data

(63) Continuation of application No. PCT/KR2023/013742, filed on Sep. 13, 2023.

(30) Foreign Application Priority Data

Nov. 17, 2022 (KR) .......... 10-2022-0154843
Jul. 6, 2023 (KR) .......... 10-2023-0087978

(51) Int. Cl.
*A61K 31/702* (2006.01)
*A61P 25/28* (2006.01)

(52) U.S. Cl.
CPC ............ *A61K 31/702* (2013.01); *A61P 25/28* (2018.01)

(58) Field of Classification Search
CPC .............................. A61K 31/702; A61P 25/28
See application file for complete search history.

(56) References Cited

U.S. PATENT DOCUMENTS

2022/0160013 A1*   5/2022   McConnell ............. A23L 33/40

FOREIGN PATENT DOCUMENTS

| KR | 10-2019-0130720 A | 11/2019 |
| KR | 10-2302304 B1 | 9/2021 |
| KR | 10-2389889 B1 | 4/2022 |
| KR | 10-2527378 B1 | 5/2023 |

OTHER PUBLICATIONS

Ossenkoppele, R. et al., JAMA, "Prevalance of Amyloid PET Positivity in Dementia Syndromes in Meta-analysis", 2015, vol. 313, No. 19, pp. 1939-1949 (Year: 2015).*

* cited by examiner

*Primary Examiner* — Bahar Craigo
(74) *Attorney, Agent, or Firm* — Sughrue Mion, PLLC

(57) ABSTRACT

Disclosed is a method for, preventing, ameliorating or treating dementia by administering a composition containing 2'-fucosyllactose. 2'-FL ameliorates brain damage caused by amyloid beta and neuroinflammation by suppressing or preventing accumulation of the amyloid beta, thus being highly effective in preventing, ameliorating and treating dementia.

2 Claims, 13 Drawing Sheets

***$p \leq 0.001$, WT-vehicle vs, #$p \leq 0.05$, 5xFAD-vehicle vs

1) CORRECT

2) INCORRECT

*p ≤ 0.05, p ≤ 0.01, *p ≤ 0.001.
5xFAD-Vehicle vs.

***$p \leq 0.001$, WT-vehicle vs, ###$p \leq 0.001$, 5xFAD-vehicle vs,
$p \leq 0.01$, 5xFAD-vehicle vs, #$p \leq 0.05$, 5xFAD-vehicle vs
control: WT-vehicle group

***$p \leq 0.001$, WT-vehicle vs, ###$p \leq 0.001$, 5xFAD-vehicle vs control: WT-vehicle group

COMPOSITION FOR AMELIORATING OR TREATING DEMENTIA CONTAINING 2'-FUCOSYLLACTOSE

CROSS REFERENCE TO RELATED APPLICATIONS

This application is a Rule 53 (b) Continuation of International Application No. PCT/KR2023/013742 filed on Sep. 13, 2023, claiming priority based on Korean Patent Application No. 10-2022-0154843 filed on Nov. 17, 2022, and Korean Patent Application No. 10-2023-0087978 filed on Jul. 6, 2023, the respective disclosures of all of the above of which are incorporated herein by reference in their entirety.

TECHNICAL FIELD

The present invention relates to a composition for preventing, ameliorating or treating dementia containing 2'-fucosyllactose, and a method for preventing, ameliorating or treating dementia by administering the composition.

BACKGROUND ART

In accordance with an aging society all over the world including Korea, increasing interest in geriatric diseases has brought about active research associated therewith. Alzheimer's disease or Alzheimer's dementia is a degenerative neurological disease in which abnormal proteins (such as amyloid beta proteins and tau proteins) that accumulate in the brain gradually destroy brain nerve cells and is one of the most common types of dementia in the elderly. Alzheimer's disease develops in 10% of people aged 65 to 74, 19% of people aged 75 to 84, and 47% of people aged 85 or older and the incidence rate thereof is increasing every year. Therefore, Alzheimer's disease is emerging as a major social problem.

Alzheimer's disease causes a very serious mental and physical burden on patients and families thereof due to the characteristics of the disease.

Neither a method of preventing Alzheimer's disease nor an early diagnosis method thereof has been established and known to date. However, the diagnosis of Alzheimer's disease has been made solely based on doctors' clinical findings and neuropsychological tests. As a result, Alzheimer's disease is diagnosed only after it has progressed significantly, thus being very difficult to treat. Drugs for treating Alzheimer's disease have been not developed yet and only drugs for relieving symptoms thereof are used.

The main symptoms of Alzheimer's disease include memory loss, decreased language skills, decreased ability to understand time and space, impaired judgment, behavioral or psychotic symptoms, depression, severe mood swings, nocturnal confusion, and auditory hallucinations or visual hallucinations. Although the exact cause and mechanism of Alzheimer's disease have not been revealed, pathways and reduced secretion of several related genes such as apolipoprotein E4 allele and neurotransmitters, old age, Down syndrome, low education, and women over 80 years of age are known as risk factors for developing Alzheimer's disease. In addition, insulin resistance, which is a major factor causing cardiovascular diseases and metabolic syndromes such as high blood pressure, diabetes, hyperlipidemia, and obesity, is emerging as another risk factor for Alzheimer's disease. These various factors cause nerve cell death due to toxic proteins such as senile plaques, neurofibrillary tangles, amyloid beta (Aβ), and APP-C proteins (anti-amyloid precursor proteins), synapse loss, and neurofibrillary tangles formed by denaturation and hyperphosphorylation of tau in the brains of Alzheimer's disease patients, and the related mechanisms thereof have been revealed.

Amyloid beta (Abeta or Aβ) is a major component of amyloid plaques found in the brains of Alzheimer's disease patients, is a peptide consisting of 36 to 43 amino acids, and is known to be produced from amyloid precursor protein (APP). In addition, neuroinflammation is considered as a cause of Alzheimer's dementia and various other diseases due to autoimmune reactions.

Accordingly, the present inventors found that 2'-fucosyllactose (2'-FL) inhibits or prevents the accumulation of amyloid beta, thereby ameliorating brain damage caused by amyloid beta and neuroinflammation. Based thereon, the present invention has been completed.

DISCLOSURE

Technical Problem

Therefore, the present invention has been made in view of the above problems, and it is one object of the present invention to provide a pharmaceutical composition for preventing or treating dementia containing 2'-FL, and a method for preventing, ameliorating or treating dementia by administering the composition.

It is another object of the present invention to provide a food composition for preventing or ameliorating dementia containing 2'-FL.

Technical Solution

In accordance with the present invention, the above and other objects can be accomplished by the provision of a pharmaceutical composition for preventing or treating dementia containing 2'-FL.

The pharmaceutical composition preferably further contains 3-fucosyllactose (3-FL).

The dementia is preferably caused by accumulation of amyloid beta.

In accordance with another aspect of the present invention, provided a food composition for preventing or ameliorating dementia containing 2'-FL.

The food composition preferably further contains 3-FL.

The dementia is preferably caused by accumulation of amyloid beta.

Advantageous Effects

2'-FL ameliorates brain damage caused by amyloid beta and neuroinflammation by suppressing or preventing accumulation of amyloid beta, thus being highly effective in preventing, ameliorating and treating dementia.

DESCRIPTION OF DRAWINGS

The above and other objects, features, and other advantages of the present invention will be more clearly understood from the following detailed description taken in conjunction with the accompanying drawings, in which.

BEST MODE

Figure 1:
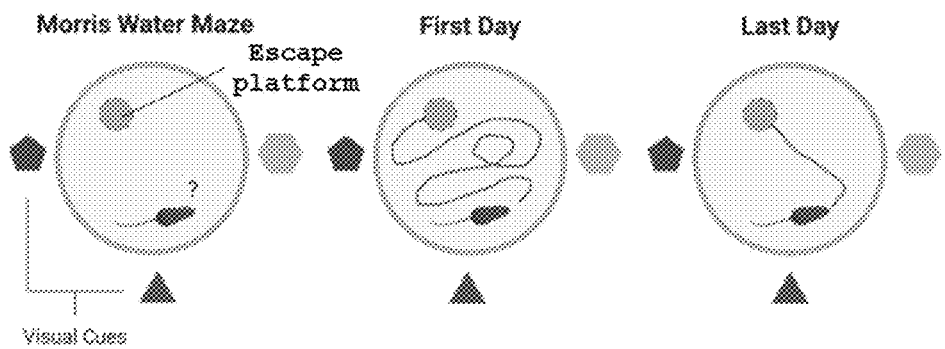
FIG. 1 is a schematic diagram illustrating a water maze test method.
Figure 1:
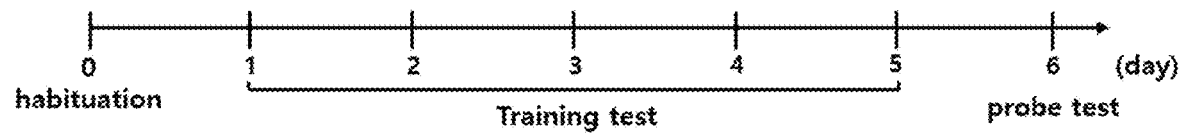

The present invention provides a pharmaceutical composition for preventing or treating dementia containing 2'-FL, and a method for preventing, ameliorating or treating dementia by administering the composition. The pharmaceutical composition preferably further contains 3-fucosyllactose (3-FL).

The present invention provides a food composition for preventing or ameliorating dementia containing 2'-FL. The food composition preferably further contains 3-FL.

2'-FL and 3-FL used herein are typical human milk oligosaccharides (HMOs) contained in breast milk.

An embodiment of the present invention shows that the 2'-FL-administered group inhibits amyloid beta accumulation and reduces blood levels of IL-6 and TNF-α, which are neuroinflammatory factors, which indicates that 2'-FL, which is a human milk oligosaccharide (HMO), is effective in preventing, treating or ameliorating dementia. The composition of the present invention, which has been found to exhibit such effects, is effective in treating dementia caused by accumulation of amyloid beta or dementia caused by neuroinflammation.

Amyloid beta (or beta-amyloid) is the main component of amyloid plaques found in the brains of Alzheimer's patients, is crucially involved in Alzheimer's disease, and is known to be composed of 36 to 43 amino acid peptides. This peptide is derived from the amyloid precursor protein, which is cleaved by beta-secretase and gamma-secretase to produce amyloid beta.

Amyloid beta molecules may aggregate to form soluble oligomers that can exist in several forms. It is expected that specific misfolded oligomers may induce misfolded oligomeric forms of other amyloid beta molecules, thus inducing a chain reaction similar to prion infection. There is evidence that the plaques thus produced are toxic to nerve cells, tau protein, which is another protein involved in Alzheimer's disease, also forms misfolded oligomers like prions, and misfolded amyloid beta may incorrectly transform tau.

Meanwhile, neuroinflammation is considered as a cause of various diseases caused by Alzheimer's dementia and autoimmune reactions. Specifically, although the chronic inflammatory response found in the brains of Alzheimer's patients was first understood to be a mechanism responding to neuronal loss, recent extensive research has shown that the increased inflammatory response is not only related to neuronal damage but also may increase amyloid beta accumulation and neurofibrillary tangles. It has been known that amyloid beta accumulation may increase neuroinflammation.

In addition, the results of the test of candidate substances with neuroinflammatory and immunomodulatory mechanisms in animal models show that the e candidate substances improve brain neuroinflammation and slow cognitive decline regardless of the degree of amyloid beta accumulation. Therefore, neuroinflammation inhibitors are emerging as novel therapeutic alternatives for Alzheimer's disease caused by neuroinflammation as well as Alzheimer's disease caused by the accumulation of amyloid beta or tau proteins.

The present invention provides a pharmaceutical composition for preventing or treating dementia containing 2'-FL, and a method for preventing, ameliorating or treating dementia by administering the composition. The dementia may preferably be caused by accumulation of amyloid beta.

As used herein, the term "prevention" refers to any action that suppresses or delays the onset of dementia by administration of the pharmaceutical composition according to the present invention.

As used herein, the term "treatment" refers to any action that ameliorates or beneficially changes symptoms due to dementia by administration of the pharmaceutical composition according to the present invention.

The composition of the present invention may further contain one or more active ingredients exhibiting the same or similar function in addition to 2'-FL.

The pharmaceutical composition of the present invention may further contain a pharmaceutically acceptable carrier in addition to 2'-FL.

The type of carrier that can be used in the present invention is not particularly limited and any carrier commonly used in the art may be used. Non-limiting examples of the carrier include lactose, dextrose, sucrose, sorbitol, mannitol, saline, sterile water, Ringer's solution, buffered saline, albumin injection solution, xylitol, erythritol, maltitol, maltodextrin, glycerol, ethanol, and the like. These may be used alone or in combination of two or more thereof.

In addition, the pharmaceutical composition of the present invention may further contain other pharmaceutically acceptable additives such as antioxidants, excipients, diluents, buffers or bacteriostats, if necessary, and may further contain surfactants, binders, fillers, extenders, wetting agents, disintegrants, dispersants or lubricants.

The 2'-FL may be contained in the pharmaceutical composition of the present invention in an amount of 0.00001 wt % to 99.99 wt %, preferably 0.1 wt % to 90 wt %, more preferably 0.1 wt % to 70 wt %, even more preferably 0.1 wt % to 50 wt %, based on the total weight of the pharmaceutical composition, but is not limited thereto, and the content of the 2'-FL may vary depending on the condition of the subject to which the composition is administered, the type of specific disease, the degree of progression of the disease, and the like. If necessary, 2'-FL may be present in an amount equal to the total amount of the pharmaceutical composition.

That is, the pharmaceutically effective amount and effective dosage of the pharmaceutical composition of the present invention may vary depending on the formulation method, administration method, administration time, and/or route of administration of the pharmaceutical composition, and may vary depending on several factors including the type and extent of the reaction that is achieved by administration of the pharmaceutical composition, the type, age, weight, general health condition, symptoms or severity of disease, gender, diet and excretion, of the subject to which the composition is administered, and the ingredients of drug or other composition administered simultaneously or sequentially to the subject, and the like, and similar factors well known in the pharmaceutical field. Those skilled in the art can easily determine and prescribe an effective dosage for the desired treatment. For example, the daily dose of the pharmaceutical composition of the present invention is about 0.0001 to 1,000 mg/kg, preferably 0.001 to 100 mg/kg, and may be administered once a day or several times a day, divided into multiple doses.

The pharmaceutical composition of the present invention may be administered once a day or several times a day, divided into multiple doses. The pharmaceutical composition of the present invention may be administered as a single therapeutic agent or in combination with other therapeutic agents, sequentially or simultaneously with conventional therapeutic agents. Taking into consideration these factors, it is important to administer the composition in the minimum amount sufficient to achieve maximum efficacy without side effects, which can be easily determined by those skilled in the art.

The pharmaceutical composition of the present invention may be used in combination with various methods such as hormone therapy and drug therapy to prevent or treat dementia.

As used herein, the term "administration" means supplying the pharmaceutical composition of the present invention to a patient using any suitable method. The route and mode of administration of the pharmaceutical composition of the present invention may be independent, and any route and mode of administration may be used without particular limitation as long as the pharmaceutical composition can reach the desired site.

The pharmaceutical composition may be administered orally or parenterally, and may be prepared and used in various formulations suitable for oral administration or parenteral administration.

Non-limiting examples of formulations for oral administration using the pharmaceutical composition of the present invention include oily suspensions, troches, lozenges, tablets, aqueous suspensions, prepared powders, granules, emulsions, hard capsules, soft capsules, syrups, elixirs, or the like.

In order to formulate the pharmaceutical composition of the present invention for oral administration, a binder such as sorbitol, mannitol, starch, amylopectin, cellulose, lactose, saccharose or gelatin, a lubricant such as magnesium stearate, calcium stearate, sodium stearyl fumarate or polyethylene glycol wax, an excipient such as dicalcium phosphate, a disintegrant such as corn starch or sweet potato starch, a fragrance, syrup, sweetener or the like may be used. Furthermore, for capsules, a liquid carrier such as fatty oil may be further used in addition to the above-mentioned substances.

The parenteral administration of the pharmaceutical composition of the present invention may be carried out by intramuscular administration, transdermal administration, intravenous administration, intraperitoneal administration, or subcutaneous administration, and the composition may be applied, sprayed, or inhaled to a diseased site, but the parenteral administration is not limited thereto.

Non-limiting examples of parenteral preparations using the pharmaceutical composition of the present invention include injections, suppositories, ointments, powders for application, oils, powders for respiratory inhalation, aerosols for sprays, creams, and the like.

In order to formulate the pharmaceutical composition of the present invention for parenteral administration, sterile aqueous solutions, non-aqueous solvents, suspensions, emulsions, lyophilizates, external preparations, and the like may be used. The non-aqueous solvents and suspensions may include vegetable oils such as olive oil, injectable esters such as propylene glycol, polyethylene glycol, ethyl oleate and the like.

When the pharmaceutical composition of the present invention is formulated into an injection solution, it is obtained by mixing the pharmaceutical composition with a stabilizer or buffer in the presence of water to prepare a solution or suspension and injecting the solution or suspension into a unit container such as an ampoule or vial.

When the pharmaceutical composition of the present invention is formulated into an aerosol, a propellant or the like may be blended with an additive so as to disperse the water-dispersed concentrate or wet powder.

When the pharmaceutical composition of the present invention is formulated into an ointment, oil, cream, powder for application, external preparation for skin, or the like, an animal oil, vegetable oil, wax, paraffin, polyethylene glycol, silicone, bentonite, silica, talc, starch, tragacanth, cellulose derivatives, or zinc oxide may be used as the carrier.

Meanwhile, the present invention provides a food composition for preventing or ameliorating dementia containing 2'-FL. The dementia is caused by accumulation of amyloid beta.

The content of 2'-FL in the food composition of the present invention is not particularly limited and may vary depending on the condition of the subject to which the composition is administered, the type of specific disease, the degree of progression of the disease, and the like. If necessary, the content of 2'-FL may be equal to the total content of the food.

The food composition of the present invention may be, for example, any one selected from noodles, gums, dairy products, ice cream, meat, grains, caffeinated beverages, general drinks, chocolate, bread, snacks, confectionery, candy, pizza, jellies, alcoholic beverages, alcohol, vitamin complexes and other health supplements, but is not limited thereto.

When the food composition of the present invention is used in the form of a food additive, it may be added alone or used in combination with other food or food ingredients, and may be appropriately used according to a conventional method.

In addition, the term "food composition" of the present invention includes health functional food. The term "health functional food" means food manufactured (including processing) with functional raw materials or ingredients beneficial to the human body according to Act No. 6727 of Health Functional Foods, and the term "functionality" means controlling nutrients for the structure or functions of the human body or providing beneficial effects to health purposes, such as physiological effects.

The food composition of the present invention may contain additional ingredients that are commonly used to improve odor, taste, appearance, and the like. For example, the food composition may contain biotin, folate, pantothenic acid, vitamins A, C, D, E, B1, B2, B6, and B12, niacin, and the like. For example, the food composition may contain minerals such as chromium (Cr), magnesium (Mg), manganese (Mn), copper (Cu), zinc (Zn), iron (Fe), and calcium (Ca). In addition, the food composition may contain amino acids such as cysteine, valine, lysine, and tryptophan. In addition, the food composition may contain food additives such as preservatives (such as potassium sorbate, sodium benzoate, salicylic acid, and sodium dehydroacetate), pigments (such as tar pigments), coloring agents (such as sodium nitrite), bleach (sodium sulfite), disinfectants (such as bleaching powder and high-grade bleaching powder, and sodium hypochlorite), expanders (such as alum and D-potassium hydrogen tartrate), reinforcers, emulsifiers, thickeners, coating agents, antioxidants (such as butylhydroxyanisole (BHA), and butylhydroxytoluene (BHT), seasonings (such as MSG), sweeteners (such as dulcin, cyclamate, saccharin, and sodium), flavorings (such as vanillin and lactones), gum bases, anti-foaming agents, solvents, enhancers, and the like. The food additives may be selected depending on the type of food and may be used in an appropriate amount.

Hereinafter, the present invention will be described in more detail with reference to the following examples. The scope of the present invention is not limited to the examples, and encompasses modifications of the technical concept equivalent thereto.

Example 1: Evaluation of Effects of 2'-FL Administration on Improvement of Brain Cognitive Function and Memory_Animal Behavior Test The experimental animals used herein were 24-week-old 5×FAD (Aβ plaques) Alzheimer's models. The experimental animals were raised at a temperature of 22±3° C., at a relative humidity of 30±10%, and at an illuminance of 150 to 300 Lux for a lighting period of 12 hours (08:00~20:00), and five or less animals were raised in each polycarbonate cage.

The feed used herein was solid feed for laboratory animals (Orient), water used herein was pre-filtered tap water, and the experiment was conducted under free diet conditions.

The distilled water (DW)-administered group was used as a negative control (vehicle), and a donepezil-administered group was used as a positive control. The term "dementia group" refers to 5×FAD mice administered distilled water and the term "normal group" refers to wild-type mice administered distilled water.

The statistical significance of all experimental results was verified using ANOVA and T-test at a significance level of $p<0.05$.

1. Water Maze Test

2'-FL was orally administered at various concentrations to wild-type and 5×FAD mouse groups for 8 weeks and then a water maze test was performed. Specifically, a circular water tank with a diameter of 150 cm and a height of 60 cm was filled to a height of 30 cm with water, and an escape platform was installed in one area of the four quadrants of the tank.

During the training period, the escape platform was placed 1 cm below the surface of the water in the tank so that it was invisible, training was repeated at the identical water entry point three times a day, and recording was performed using a video tracking system (SMART v3.0 panlab SL). When the experimental animal reached the escape platform within 60 seconds, it was allowed to stay on the escape platform for 15 seconds, and when it could not find the escape platform, it was guided to the escape platform by hand and trained to stay on the escape platform alone for 20 seconds.

In the probe test on the 6th day, the escape platform was removed and the experimental animals were allowed to swim freely for 60 seconds. At this time, the time (sec) to first reach the location of the escape platform and the number of target crossings were recorded (FIG. 1). FIG. 1 is a schematic diagram illustrating the water maze test method.

Figure 2:
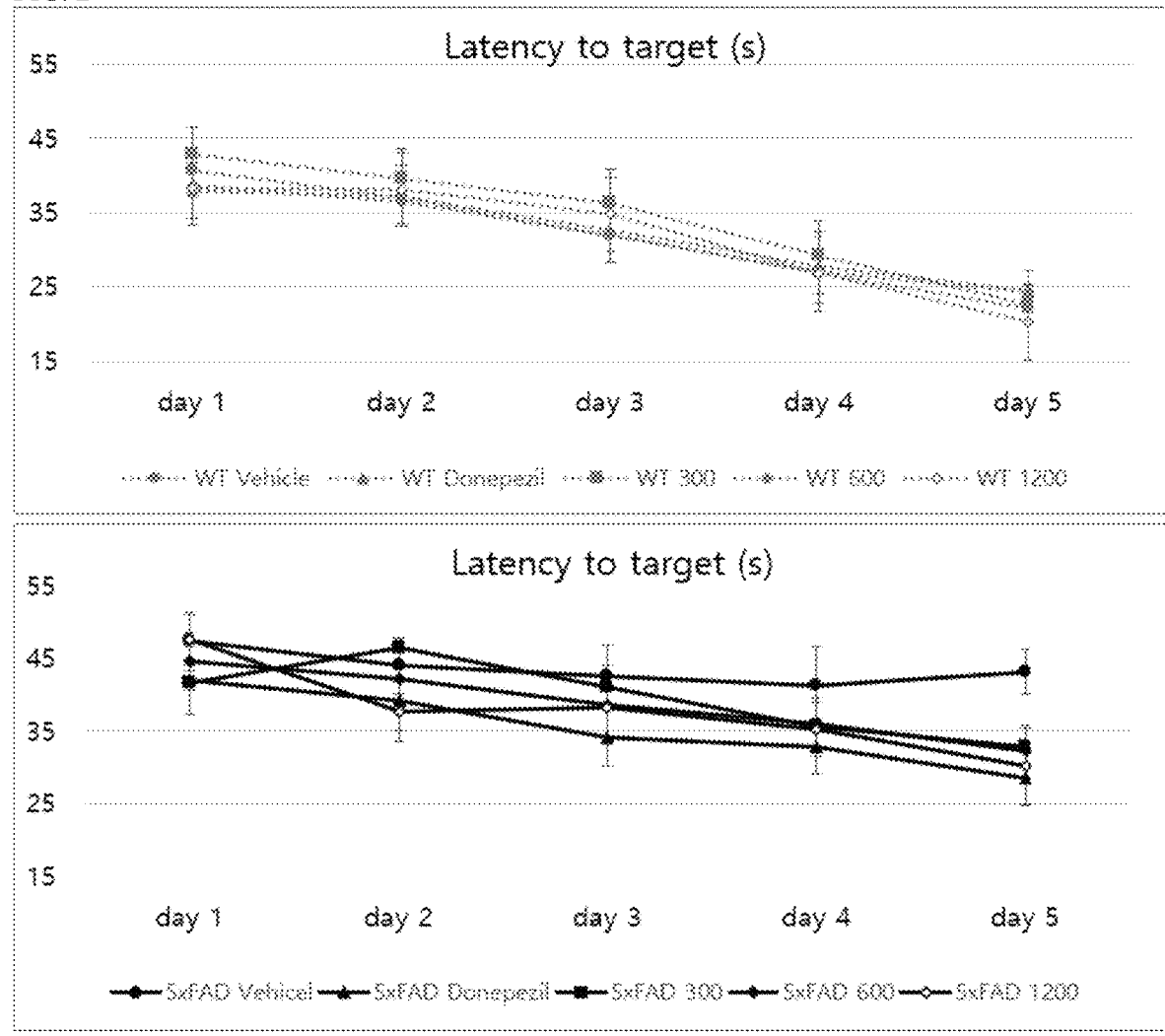
FIG. 2 shows the effect of administration of 2'-FL on spatial memory formed through water maze training, determined by measurement of the change in arrival time at the escape platform on each day.
Figure 3:
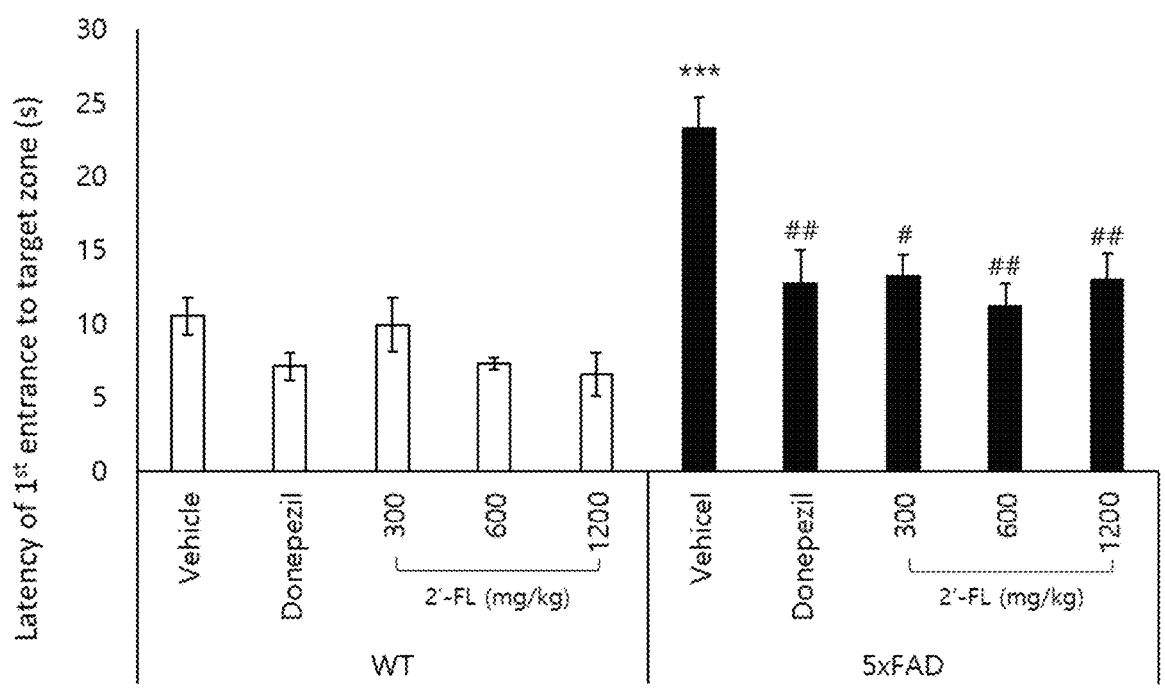
FIG. 3 shows the effect of administration of 2'-FL on spatial memory formed through water maze training, confirmed by measuring the arrival time in the zone including the escape platform on the 5$^{th}$ day of water maze training.

The result of the test showed that the dementia group exhibited significantly increased time to find escape platform, as compared to the normal group. However, both the normal and dementia groups reduced the time to arrive at the escape platform during the water maze training period through 2'-FL administration, compared to distilled water (vehicle) administration, which indicates that the administration of 2'-FL resulted in formation of spatial memory through training in the dementia and normal groups (FIGS. 2 and 3). FIG. 2 shows the effect of administration of 2'-FL on spatial memory formed through water maze training, determined by measurement of the change in arrival time at the escape platform on each day and FIG. 3 shows the effect of administration of 2'-FL on spatial memory formed through water maze training, confirmed by measuring the arrival time in the zone including the escape platform on the $5^{th}$ day of water maze training. In other words, the result in FIG. 2 was obtained by measuring the time of arrival at the exact target spot, and the result of FIG. 3 was obtained by measuring the time of arrival in a zone with a certain radius including the target spot, so that there may be a slight time difference between the two results.

Figure 4:
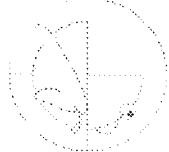
FIG. 4 shows the effect of administration of 2'-FL on spatial memory formed through water maze training, confirmed by measuring the escape platform arrival route on the 5$^{th}$ day of water maze training.

In addition, the result of confirmation of the arrival route to the escape platform on the $5^{th}$ day of water maze training showed that the arrival route to the escape platform was simplified, especially in the 2'-FL-administered dementia group compared to the dementia group (FIG. 4). FIG. 4 shows the effect of administration of 2'-FL on spatial memory formed through water maze training, confirmed by measuring the escape platform arrival route on the $5^{th}$ day of water maze training.

Overall, it can be seen from the foregoing that the 2'-FL-administered group of all concentrations, especially the 2'-FL-administered dementia group, had significantly improved spatial memory through training, compared to the dementia group.

2. Y-Maze Test

2'-FL was orally administered at various concentrations to wild-type and 5×FAD mouse groups for 8 weeks, and then a Y-maze test was performed. The device used in the Y-maze test included three arms. The length of each arm was 42 cm, the width was 3 cm, the height was 12 cm, and the folding angle of the three arms was designed to be 120°. All test devices were made of white polyvinyl plastic.

Figure 5:
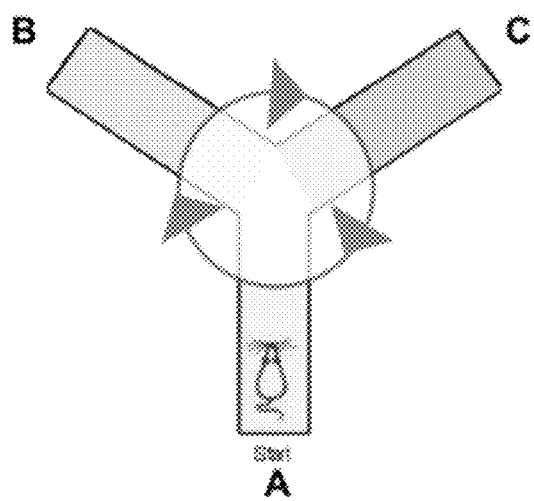
FIG. 5 is a schematic diagram illustrating the Y-maze test method, wherein (1) represents a normal cognitive function and memory behavior group and (2) represents an abnormal cognitive function and memory behavior group.
Figure 5:
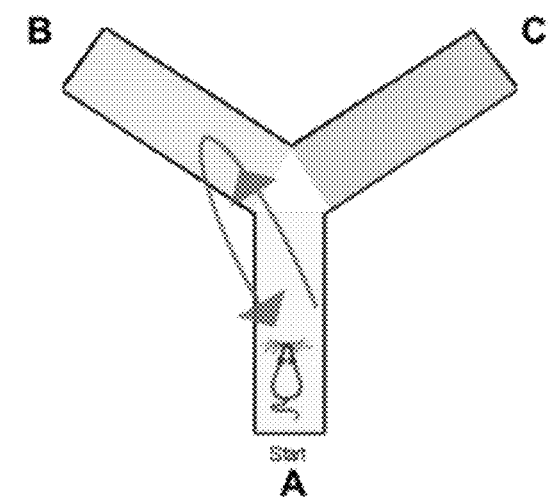

Specifically, the arms of the Y-maze were randomly designated as A, B, and C, the mouse was placed on one arm and allowed to move freely for 5 minutes, and then the arm where the mouse entered was recorded. This record was limited to cases where the tail thereof completely entered, and cases where it entered the same arm again were also recorded (FIG. 5). FIG. 5 is a schematic diagram illustrating the Y-maze test method wherein (1) represents a normal cognitive function and memory behavior group, and (2) represents an abnormal cognitive function and memory behavior group.

The case where the mouse entered three different arms one after another was given one point (actual alteration). Alteration behavior is defined as a case where the mouse enters all of three arms in turn and the result was calculated in accordance with Equation 1 below (maximum change: total number of entries—2).

$$\text{Alteration behavior (\%)} = \frac{\text{Actual alternation}}{\text{Maximum alternation}} \times 100 \quad \text{[Equation 1]}$$

Figure 6:
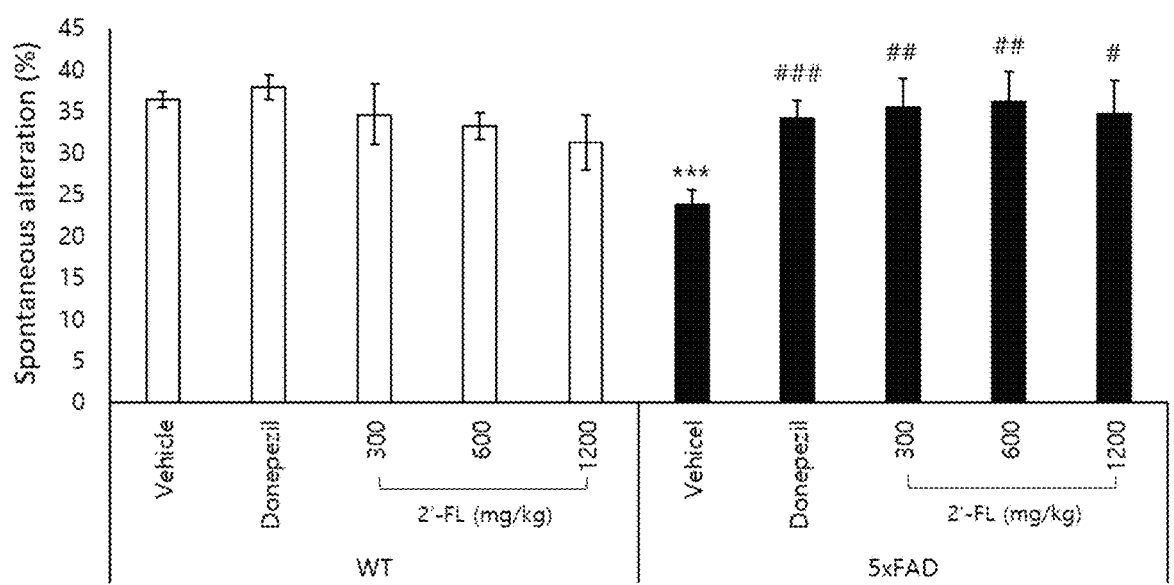
FIG. 6 shows the effect of administration of 2'-FL on short-term memory in dementia-induced rats, confirmed through the Y-maze test.

The result of the test showed that the dementia group had significantly lower spontaneous alteration (SA) than the normal group, which indicates that short-term memory was significantly deteriorated in the dementia group. On the other hand, the 2'-FL-administered dementia group exhibited significantly increased SA compared to the dementia group, which indicates that the 2'-FL-administered dementia group at all concentrations exhibited improved short-term memory and cognitive ability, compared to the dementia group (mean±SEM (n=8~12), FIG. 6). FIG. 6 shows the result of the Y-maze test, confirming the effect of administration of 2'-FL on short-term memory in dementia-derived rats.

Example 2: Evaluation of Effects of 2'-FL Administration on Improvement of Brain Cognitive Function and Memory_Molecular Marker Test The experimental animals used herein were 24-week-old 5×FAD (Aβ plaques) Alzheimer's models. The experimental animals were raised at a temperature of 22±3° C., at a relative humidity of 30±10%, and at an illuminance of 150 to 300 Lux for a lighting period of 12 hours (08:00~20:00), and five or less animals were raised in each polycarbonate cage.

The feed used herein was solid feed for laboratory animals (Orient), water used herein was pre-filtered tap water, and the experiment was conducted under free diet conditions.

The distilled water (DW)-administered group was used as a negative control (vehicle), and a donepezil-administered group was used as a positive control. The term "dementia group" refers to 5×FAD mice administered distilled water, and the term "normal group" refers to wild-type mice administered distilled water.

The statistical significance of all experimental results was verified using ANOVA and T-test at a significance level of $p<0.05$.

1. Amyloid Beta Accumulation Analysis

For the amyloid beta accumulated in mouse brain tissue, brain tissue over 1 mm in size was made transparent using a tissue transparency technique, stained with thioflavin, imaged in three dimensions, and then quantified as plaques for each brain region using the Imaris program.

Figure 7:
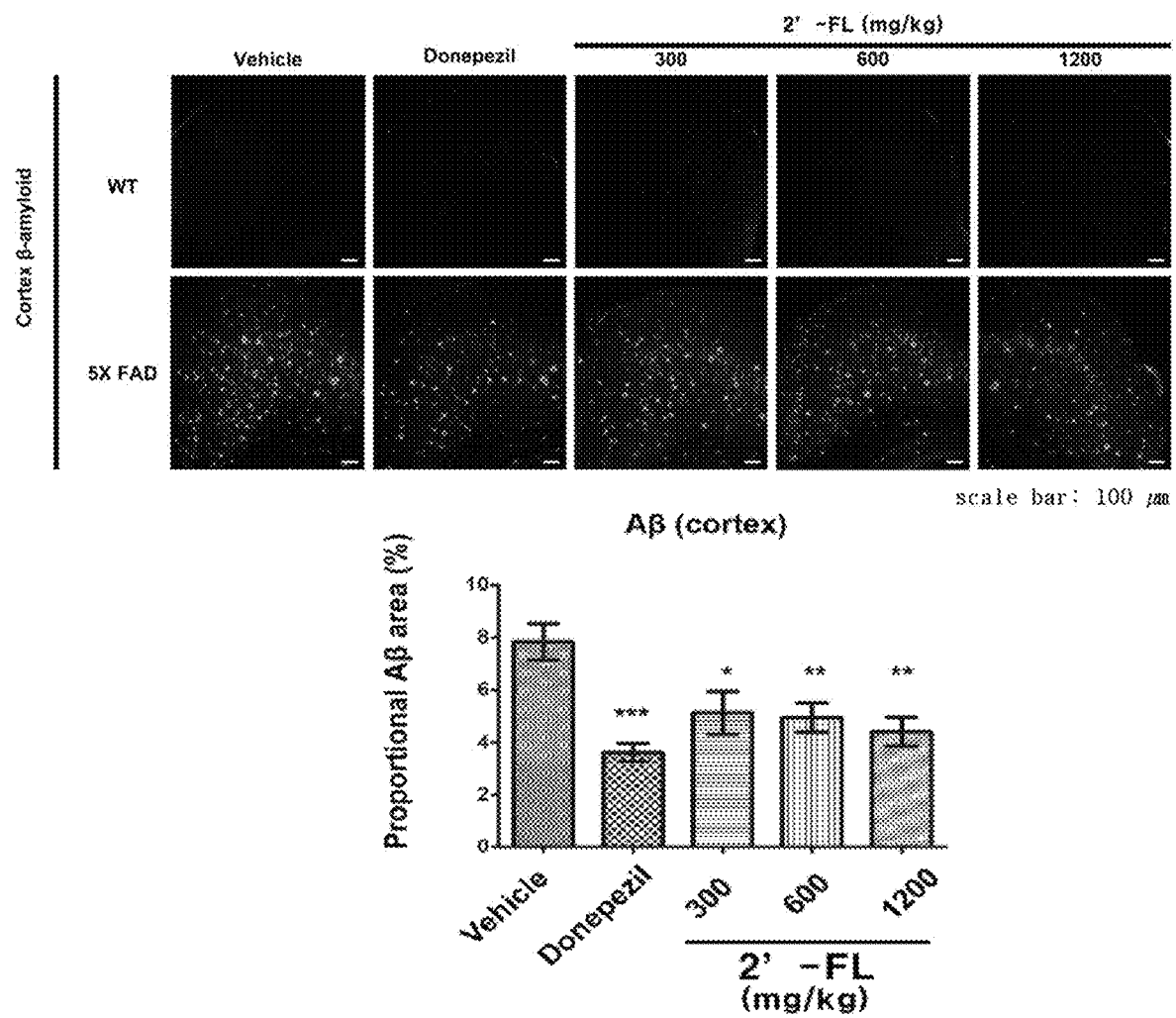
FIG. 7 shows the effect of administration of 2'-FL on reduction of amyloid beta accumulated in the brain cortex of dementia-induced rats.
Figure 8:
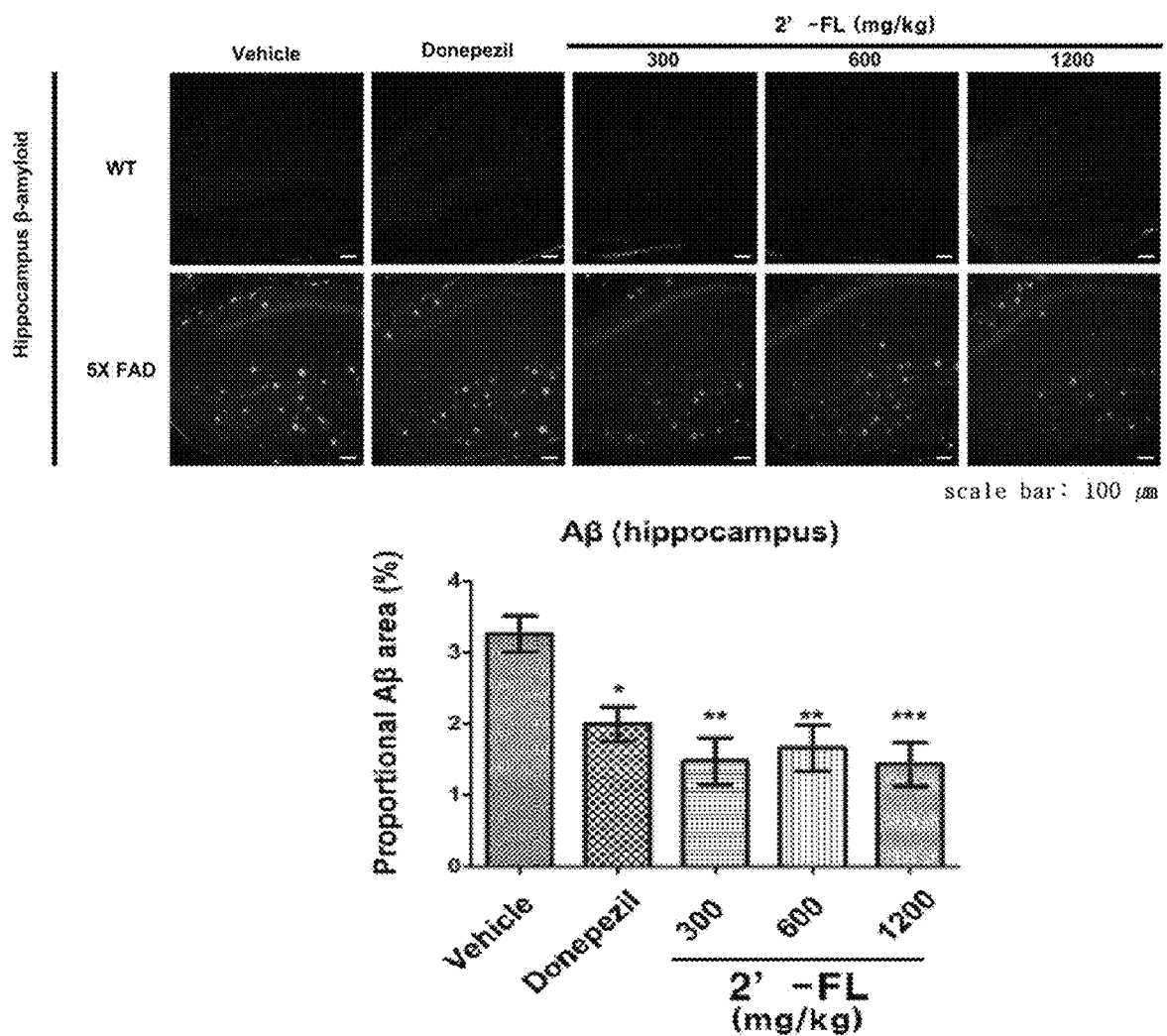
FIG. 8 shows the effect of administration of 2'-FL on reduction of amyloid beta accumulated in the brain hippocampus of dementia-induced rats.

The result of the test showed that amyloid beta accumulation was observed in both the brain cortex and hippocampus of the dementia group, and a decrease in amyloid beta accumulation was observed by administration of 2'-FL (scale bar: 100 μm; mean±SEM (n=8-12), FIGS. 7 and 8). FIG. 7 shows the effect of administration of 2'-FL on reduction of amyloid beta accumulated in the brain cortex of dementia-induced rats and FIG. 8 shows the effect of administration of 2'-FL on the reduction of amyloid beta accumulated in the brain hippocampus of dementia-induced rats.

Figure 9:
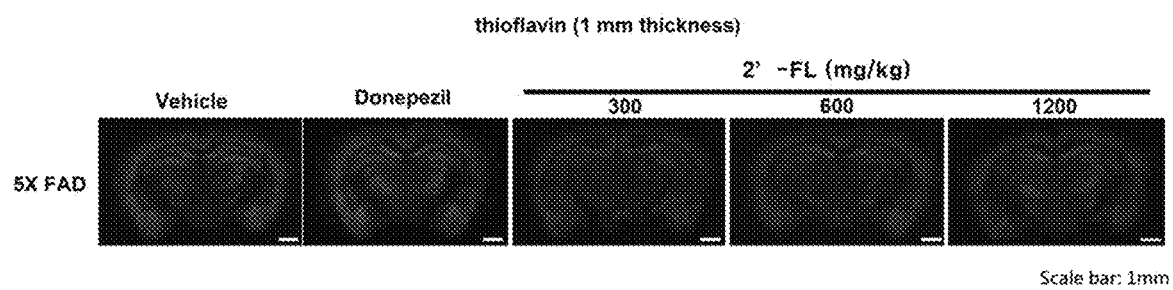
FIG. 9 is an image of the brain tissue first collected among three brain tissues collected, showing the effect of administration of 2'-FL on inhibition of amyloid beta accumulated throughout the brain of dementia-induced rats.

In addition, three 1 mm-thick brain tissues were collected from each group, the volumes thereof were measured, and the total number of accumulated amyloid beta was measured. The result showed that the accumulation of amyloid beta throughout the brain in the dementia group was significantly inhibited by administration of 2'-FL (Table 1, FIG. 9). FIG. 9 is an image of the brain tissue first collected among three brain tissues collected, showing the effect of administration of 2'-FL on inhibition of amyloid beta accumulated throughout the brain of dementia-induced rats.

Overall, the test results described above show that 2'-FL is highly effective in treating and ameliorating dementia caused by accumulation of amyloid beta.

TABLE 1

| Group | Vehicle | | | | | Donepezil | | |
|---|---|---|---|---|---|---|---|---|
| | 1st brain tissue | 2nd brain tissue | 3rd brain tissue | Avr. | SEM | 1st brain tissue | 2nd brain tissue | 3rd brain tissue |
| Volume (mm³) | 2.6E+10 | 2.6E+10 | 2.6E+10 | 2.6E+10 | 0.00 | 2.6E+10 | 2.7E+10 | 2.7E+10 |
| Ab number | 44800 | 64900 | 59600 | 56433 | 6015 | 20000 | 50500 | 40500 |
| Ab number/volume | 17034 | 19489 | 18226 | 18250 | 709 | 7547 | 18364 | 14945 |

| Group | Donepezil | | 2'-FL 300 | | | | |
|---|---|---|---|---|---|---|---|
| | Avr. | SEM | 1st brain tissue | 2nd brain tissue | 3rd brain tissue | Avr. | SEM |
| Volume (mm³) | 2.7E+10 | 3.33E+8 | 2.8E+10 | 2.8E+10 | 3.4E+10 | 3.0E+10 | 2.0E+9 |
| Ab number | 37000 | 8977 | 23900 | 26900 | 42000 | 30933 | 5601 |
| Ab number/volume | 13618 | 3192 | 8628 | 9642 | 12174 | 10148* | 1054 |

TABLE 1-continued

| | 2'-FL 600 | | | | | 2'-FL 1200 | | | | |
| --- | --- | --- | --- | --- | --- | --- | --- | --- | --- | --- |
| Group | 1st brain tissue | 2nd brain tissue | 3rd brain tissue | Avr. | SEM | 1st brain tissue | 2nd brain tissue | 3rd brain tissue | Avr. | SEM |
| Volume (mm$^3$) | 2.7E+10 | 3.2E+10 | 3.6E+10 | 3.2E+10 | 2.6E+9 | 3.2E+10 | 4.1E+10 | 3.1E+10 | 3.5E+10 | 3.18E+9 |
| Ab number | 32000 | 38400 | 20800 | 30400 | 5143 | 34300 | 31900 | 37000 | 34400 | 1473 |
| Ab number/volume | 11722 | 11852 | 5762 | 9778* | 2009 | 10719 | 7800 | 12092 | 10203* | 1266 |

*$p \leq 0.05$, Vehicle vs.
Avr. = Average (Mean)
SEM = Standard Error of the Mean

2. Tau Protein Hyperphosphorylation Analysis

Hyperphosphorylation (p-tau) of tau protein was analyzed through image observation based on immunohistochemistry (IHC) using an antibody that detects tau protein expressed in mouse brain tissue and phosphorylated tau protein.

Figure 10:
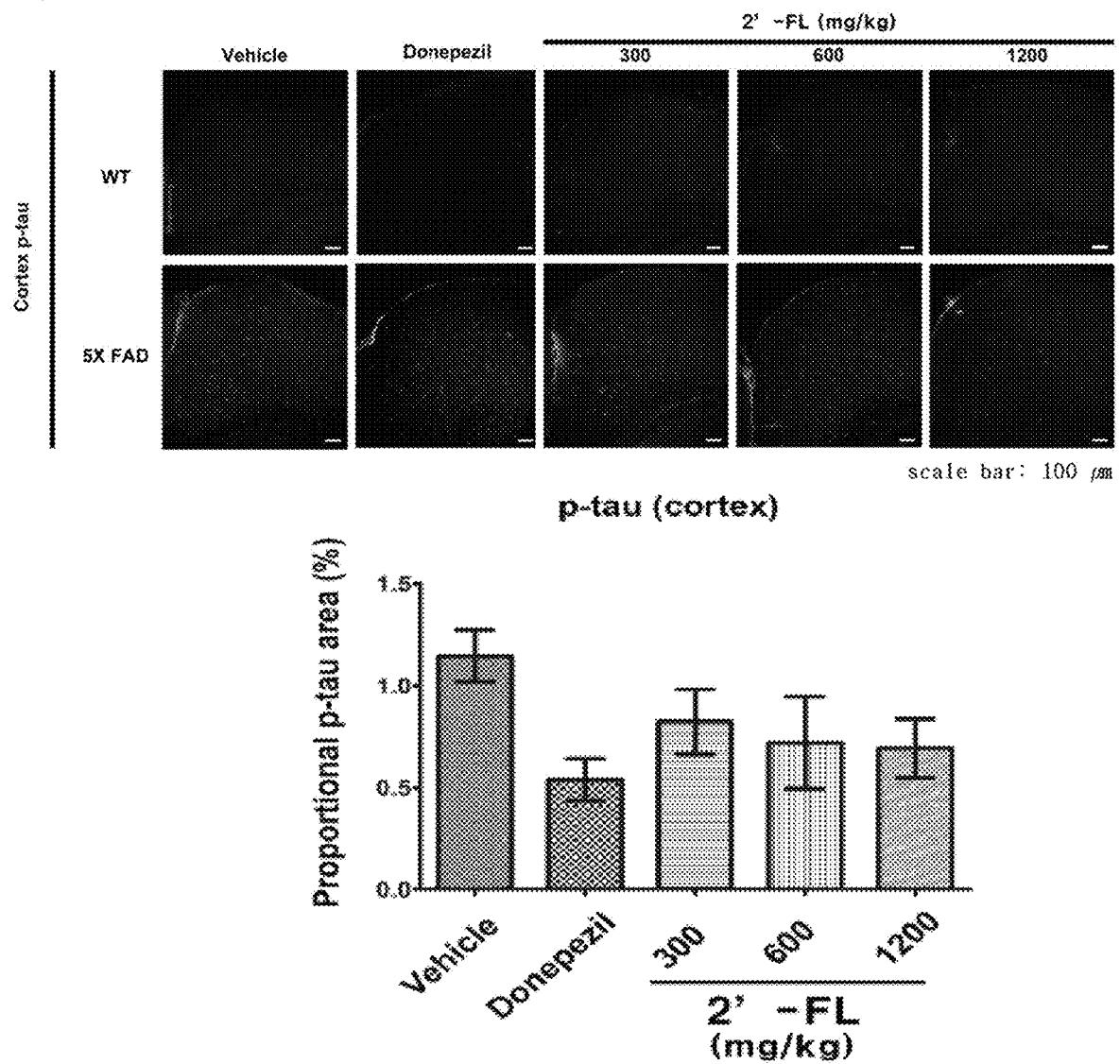
FIG. 10 shows the effect of administration of 2'-FL on inhibition of hyperphosphorylation of tau protein in the brain cortex of dementia-induced rats.
Figure 11:
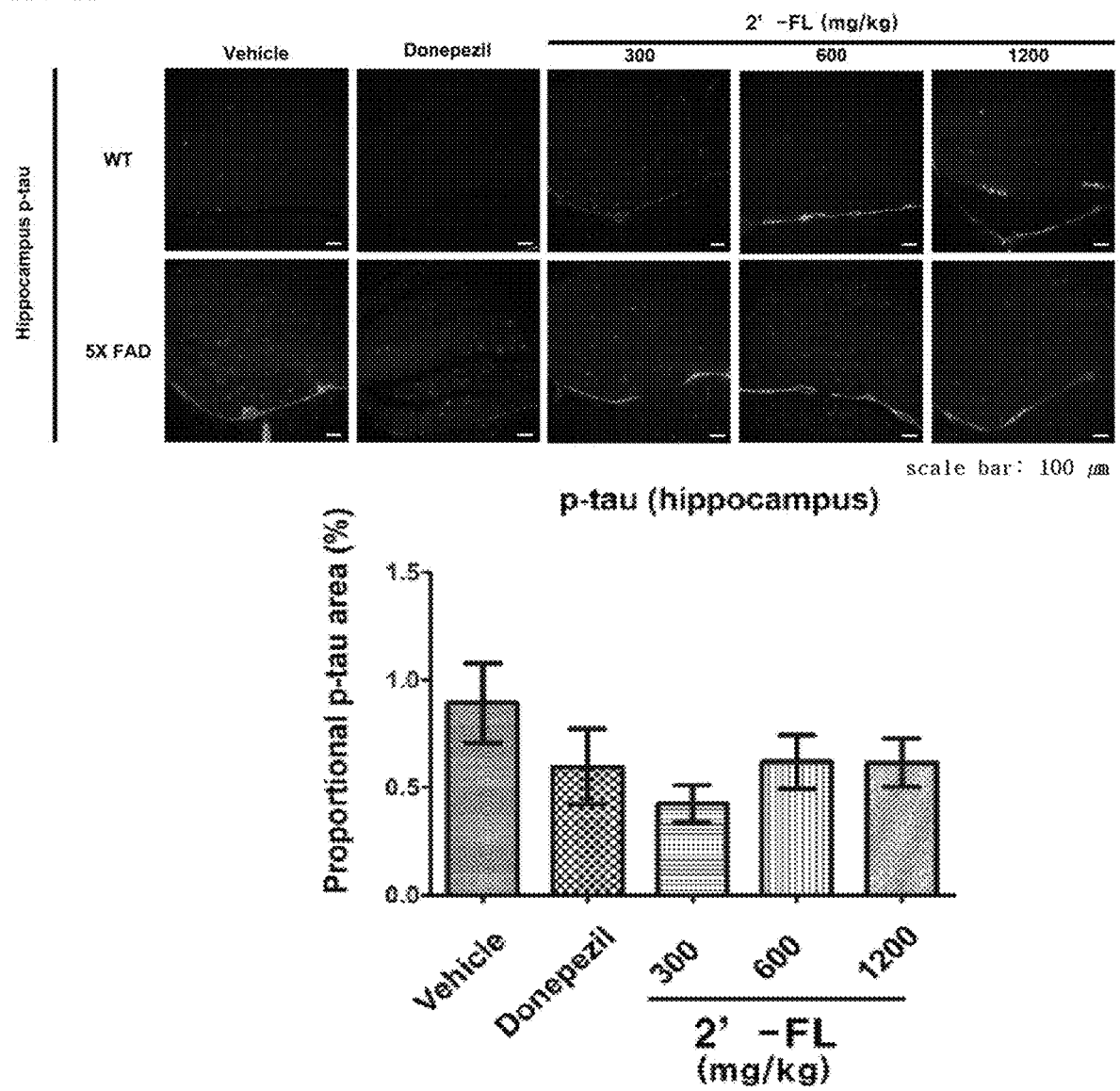
FIG. 11 shows the effect of administration of 2'-FL on inhibition of hyperphosphorylation of tau protein in the brain hippocampus of dementia-induced rats.

The result of the showed that test hyperphosphorylation of tau protein was observed in both the brain cortex and hippocampus of the dementia group. However, unlike in the amyloid beta accumulation analysis, it was found that administration of 2'-FL had no significant effect on inhibition of tau protein hyperphosphorylation (scale bar: 100 μm; mean±SEM (n=8~12), FIGS. 10 to 11). FIG. 10 shows the effect of administration of 2'-FL on inhibition of hyperphosphorylation of tau protein in the brain cortex of dementia-induced rats. FIG. 11 shows the effect of administration of 2'-FL on inhibition of hyperphosphorylation of tau protein in the hippocampus of dementia-induced rats.

3. Neuroinflammatory Marker Analysis

The concentrations of neuroinflammatory cytokines, TNF-α and IL-6 in mouse brain tissue homogenates were analyzed using enzyme-linked immunosorbent assay (ELISA).

Figure 12:
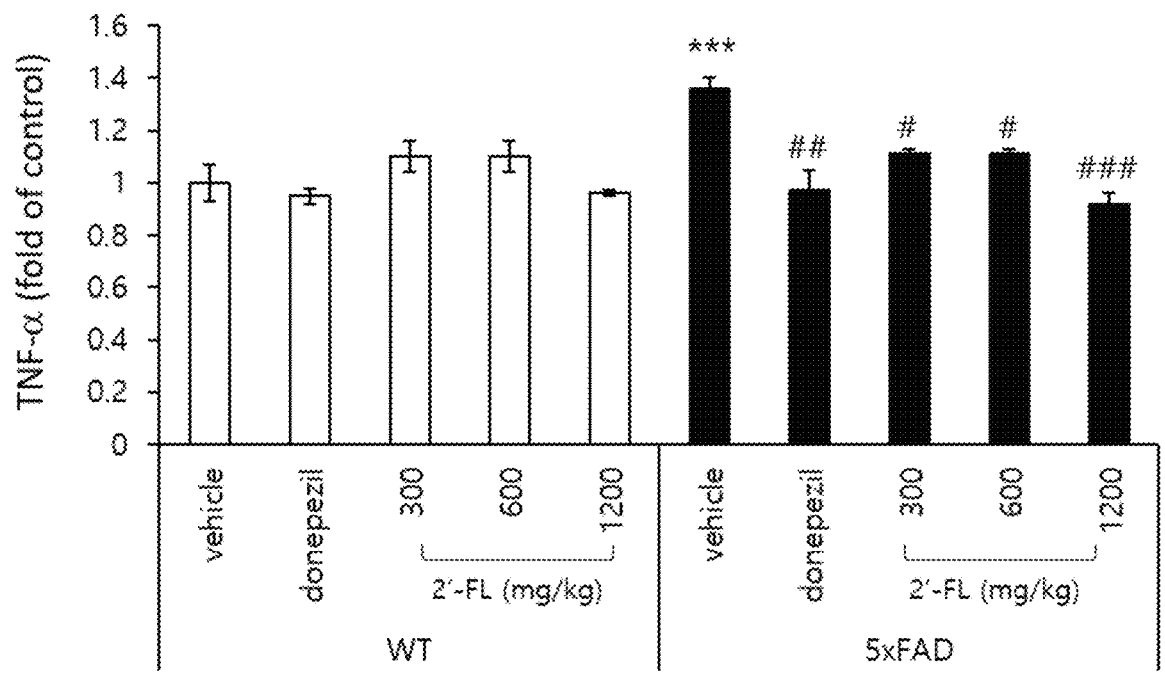
FIG. 12 shows the effect of administration of 2'-FL on reduction of blood TNF-α concentration in dementia-induced rats.
Figure 13:
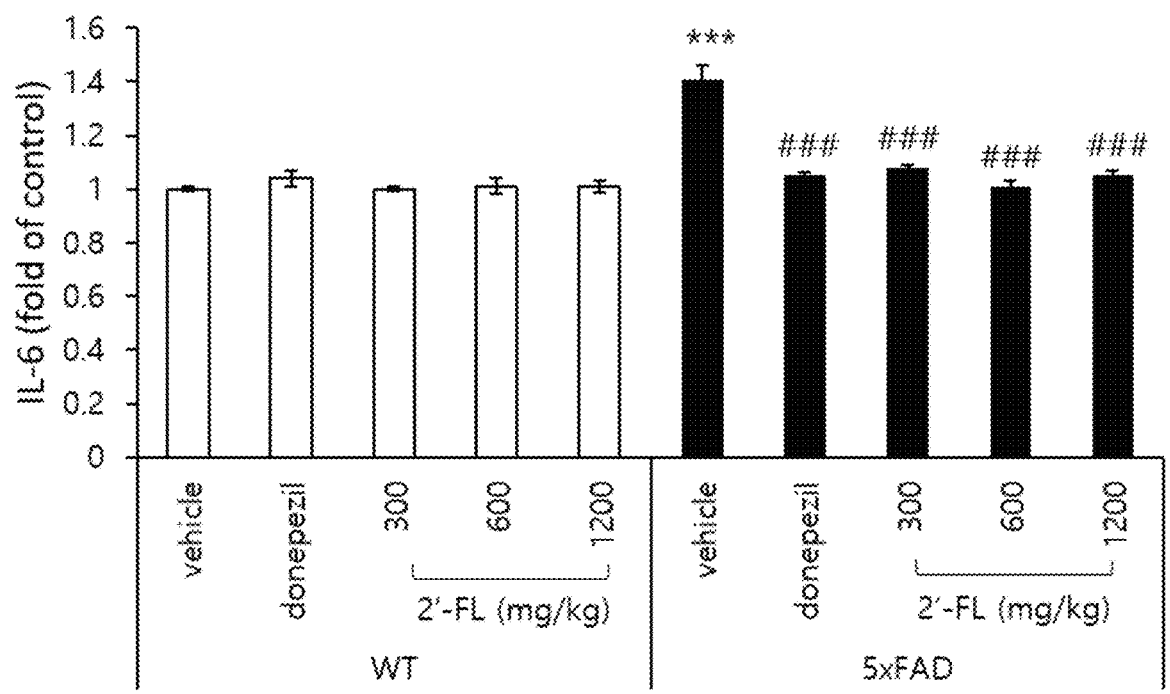
FIG. 13 shows the effect of administration of 2'-FL on reduction of the concentration of IL-6 in dementia-induced rats.

The result of the test showed that the concentration of TNF-α and IL-6 in the blood of the dementia group significantly increased, while the concentration of TNF-α and IL-6 in the 2'-FL-administered dementia group significantly decreased compared to the dementia group, which indicates that 2'-FL effectively ameliorates neuroinflammation (FIGS. 12 and 13). FIG. 12 shows the effect of administration of 2'-FL on reduction of blood TNF-α concentration in dementia-induced rats. FIG. 13 shows the effect of administration of 2'-FL on reduction of the concentration of IL-6 in dementia-induced rats.

Overall, the test results described above show that 2'-FL is highly effective in treating and ameliorating dementia caused by neuroinflammation.

The invention claimed is:

1. A method for ameliorating or treating Alzheimer's dementia caused by accumulation of amyloid beta and neuroinflammation, comprising administering to a subject in need thereof a composition comprising 2'-fucosyllactose (2'-FL),
   wherein the 2'-fucosyllactose (2'-FL) is orally administered at a daily dosage of 300 mg/kg to 1,200 mg/kg.
2. The method according to claim 1, wherein the composition further comprises 3-fucosyllactose (3-FL).

* * * * *